United States Patent [19]

Schwartz et al.

[11] 4,357,668
[45] Nov. 2, 1982

[54] BASE LINE CORRECTION METHOD AND APPARATUS

[75] Inventors: Arnold Schwartz, Bridgeport; Edward B. Delany, Ridgefield, both of Conn.

[73] Assignee: The Perkin-Elmer Corp., Norwalk, Conn.

[21] Appl. No.: 127,022

[22] Filed: Mar. 4, 1980

[51] Int. Cl.³ .................................... G01N 31/08
[52] U.S. Cl. ............................ 364/497; 73/23.1; 364/571
[58] Field of Search ............ 364/497, 498, 571, 900; 73/23.1

[56] References Cited

U.S. PATENT DOCUMENTS

| | | | |
|---|---|---|---|
| 3,475,600 | 10/1969 | Spence | 364/497 |
| 3,506,618 | 4/1970 | Smith | 364/497 |
| 3,634,868 | 1/1972 | Pelavin et al. | 364/571 |
| 3,641,444 | 2/1972 | Watts | 364/571 |
| 3,733,474 | 5/1973 | Edwards et al. | 73/23.1 |
| 3,920,970 | 11/1975 | Slaker | 364/571 |
| 4,043,756 | 8/1977 | Sommervold | 364/571 |
| 4,099,240 | 7/1978 | Rode et al. | 364/571 |
| 4,193,039 | 3/1980 | Massa et al. | 364/571 |
| 4,216,419 | 8/1980 | Van Dam et al. | 364/571 |

OTHER PUBLICATIONS

Hendrickson et al.; "Design of a Microprocessor-Based Data System for Chromatography"; *Lab;* vol. 7, No. 9, Sep. 1975; pp. 100–107.

*Primary Examiner*—Errol A. Krass
*Attorney, Agent, or Firm*—S. A. Giarratana; F. L. Masselle; R. A. Hays

[57] ABSTRACT

In a solvent gradient liquid chromatography system, base line shift is compensated by operating the system in a calibrate cycle with a desired solvent gradient program while subtracting and recording in digital form correction factors sufficient to maintain a flat base line at timed intervals during the program, and then successively recalling said digital correction factors at corresponding time intervals during a run cycle with a test sample and converting the correction factors to analog form and subtracting the converted correction factors from the system output signal for base line correction.

3 Claims, 4 Drawing Figures

UNCORRECTED CHROMATOGRAM

TIME

CORRECTED CHROMATOGRAM

TIME

BASE LINE CORRECTION METHOD AND APPARATUS

BACKGROUND OF THE INVENTION

The present invention relates to a method and apparatus which is particularly useful in correcting for base line shift in liquid chromatography during a solvent gradient run when the proportions of constituent solvents are changed.

One of the most useful liquid chromatography techniques has been found to be a solvent gradient scan in which the proportions of constituent solvents are changed in a predetermined program. This is usually carried out while employing an unchanging wavelength of illumination. The process is sometimes referred to as "gradient elution". One of the solvents is usually a weak solvent, and the other a strong solvent, for the sample materials, resulting in a clear separation of the different constituents of the sample. Such techniques, and the strong benefits of such techniques are described, for instance, in INTRODUCTION TO MODERN LIQUID CHROMATOGRAPHY by L. R. Snyder and J. J. Kirkland published in 1974 by John Wiley & Sons, Inc.

In the practice of gradient elution, it has now become common to provide for a programmed change in the proportions of the different eluants (solvents) in order to improved one or more aspects of the system performance in terms of achieving separation of different sample components.

For this purpose, liquid chromatograph machines are now commercially available which can be programmed to provide highly reproducible solvent flow proportions in a predetermined program. A machine of this type which is available, for instance, from the Perkin-Elmer Corporation of Norwalk, Conn. under the model designation Series 3B is capable of being programmed in as many as five different segments, each segment being programmable to provide for a linear variation of solvents with time, or with concave or convex characteristic gradients. All of the segments of the program are completely reproducible.

Descriptions of liquid flow control systems which are especially useful in liquid chromatographs for obtaining reproducible programmable variations of solvents with time are to be found in various U.S. patents including U.S. Pat. No. 4,084,246, issued on Apr. 11, 1978 in the name of the present inventor andassigned to the same assignee as the present invention, U.S. Pat. No. 4,032,445 issued on June 28, 1977 to Minor M. Munk for a LIQUID CHROMATOGRAPHY PUMPING SYSTEM WITH COMPENSATING MEANS FOR LIQUID COMPRESSIBILITY, and U.S. Pat. No. 4,066,879 issued Jan. 3, 1978 to Leaver and Dudley for a MEANS AND METHOD FOR CONTROLLING ELUANT GRADIENT IN LIQUID CHROMATOGRAPHY.

One of the major limitations of the eluant gradient program in the past has been that it is often desirable to use one solvent which has a much higher optical absorbency for the wavelength of light which is desired to be used than does the other solvent. This results in an extreme shift in the base line as the solvent gradient program proceeds. In some instances, the base line shift is so great that it exceeds the sample signals. Without base line correction, this can mean that some desired solvents really cannot be used with certain wavelengths of light for which they are highly absorbent. The uncorrected chromatogram illustrated in FIG. 3 of the drawings, and discussed more fully below, illustrates an example of this problem.

Previous efforts have been made to correct for base line error problems of this kind in similar instruments. For instance, see U.S. Pat. No. 4,084,248 for a METHOD AND APPARATUS FOR ERROR CORRECTION issued to Larkin B. Scott on Apr. 11, 1978 and assigned to the same assignee as the present application. However, the system disclosed in that patent is not particularly adapted to solvent gradient chromatography, and the corrections provided by that patent are limited in slope so that it is questionable whether the system of that patent would adequately correct for the extreme base line errors encountered in solvent gradient chromatography.

Accordingly, it is an important object of the present invention to provide a base line correction method and apparatus which is especially adapted to solvent gradient liquid chromatography and which is capable of providing corrections at a steep slope (rapidly changing signal level) when necessary.

It is another object of the present invention to provide a base line correction method and apparatus which is generally more efficient and more economical and more effective than prior systems of this kind.

Another object of the invention is to provide a base line drift offset correction for all of the base line correction signals for each sample run to compensate for drift of the system output.

Further objects and advantages of the invention will be apparent from the following description and the accompanying drawings.

BRIEF DESCRIPTION

In carrying out the invention there is provided a method for compensating for base line shift in liquid chromatography during a solvent gradient run as the proportions of constituent solvents are changed, comprising the steps of operating a liquid chromatography system in a calibrate cycle with a desired solvent gradient versus time interval program without a test sample while subtracting and measuring and recording in digital form correction factors at timed intervals during the solvent gradient program, said correction factors representing the corrections needed at each of said timed intervals to maintain a flat base line, and then operating the liquid chromatography system in a run cycle with a test sample and with the same solvent gradient versus time interval program while successively recalling said digital correction factors at corresponding timed intervals and converting said correction factors to analog form and subtracting said converted correction factors from the system output signal for base line correction.

DETAILED DESCRIPTION

Figure 1:
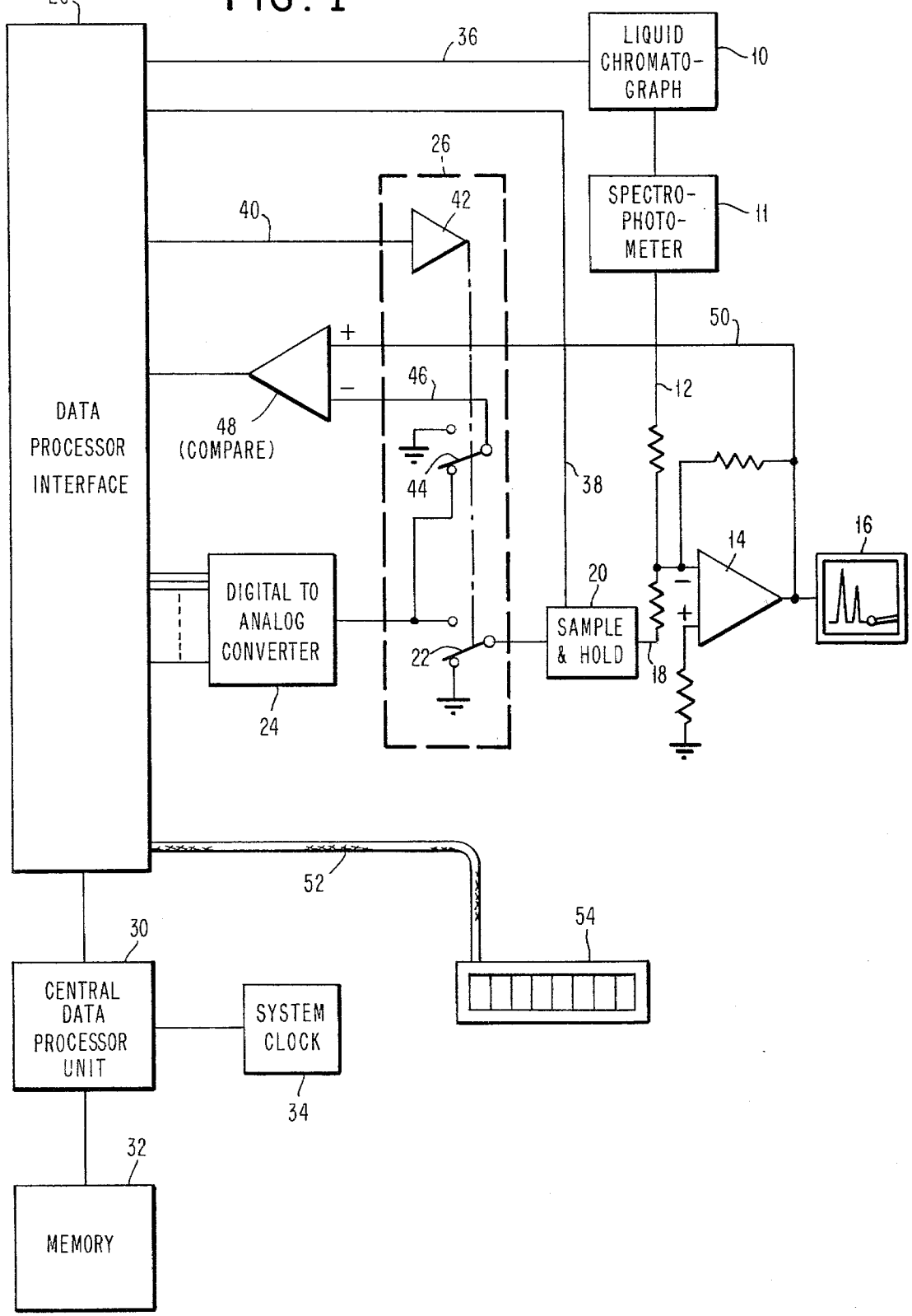
FIG. 1 is a schematic diagram of a system in accordance with the present invention.

Referring more particularly to FIG. 1, which is a schematic diagram of the apparatus of the invention, there is shown a liquid chromatograph at 10 to which is attached a dedicated spectrophotometer 11 which provides output signals in line 12 to an operational amplifier 14, the output of which is supplied to a chart recorder 16 for recordation and display. The liquid chromatograph 10 is of the type described above which can be programmed to provide reproducible flow control programs.

Base line correction signals are subtracted from the signals from the spectrophotometer 11 by application at the other input 18 of the operational amplifier 14, which is connected to operate as an offsetting amplifier. The base line correction signals are supplied through connection 18 from a sample-and-hold circuit 20 and a switch 22 from a digital-to-analog converter 24. Switch 22 comprises a part of a multiple contact electronic switch unit 26. During the operation just described, when correction signals are supplied through switch 22 from the digital-to-analog converter 24 to the sample-and-hold circuit 20, the switch 22 is shifted to its upper contact, rather than connected to ground as shown in the drawing. The correction signals obtained from the digital-to-analog converter are based upon previously stored digital values which are supplied to converter 24 through a data processor interface unit 28 and a central data processor unit 30 from a digital data memory 32 under the control of a system clock 34.

The digital correction values are read out of the memory 32 to provide new base line correction signals at predetermined intervals which may vary from about ½ second to about three seconds depending upon the total length of the solvent gradient program. While other intervals and a greater or lesser number of base line correction signals can be used, it has been found to be quite satisfactory to provide for approximately 2,000 base line correction signals over the total duration of the solvent gradient program. Thus, ½ second intervals may be used for a 16.5 minute program, one second intervals may be used for a 33 minute program, 2 second intervals may be used for a 66 minute program, and 3 second intervals may be used for a 99 minute program.

The timing of the read-out from memory 32 of the base line correction values is determined by the system clock 34. A start signal is provided from the chromatograph 10 through a connection 36 and through the data processor interface 28 to the central data processor unit 30 to synchronize the system clock 34 with the operation of the solvent gradient program.

The timing of the operation of the sample-and-hold circuit 20 is under the control of the data processor through the data processor interface 28 and control connection 38. Similarly, the switch unit 26 is operated under the control of the data processor 30 through the data processor interface 28 and connection 40 which feeds a logic gate 42 which controls the switch lever 22 and a second switch lever 44. While mechanical switch levers are schematically illustrated, it will be understood that the switches are electronic.

Since the correction signals are supplied to the sample-and-hold circuit 20 only every ½ second, or at even longer intervals, the data processing system including the central data processor unit 30, the memory 32, and the system clock 34 are time shared for other functions (time multiplexed) which are not described here and are not directly concerned with the present invention, and these components are also time multiplexed in other features of operation of the present invention as described immediately below.

As each base line correction signal is received through the digital-to-analog converter 24 to the sample-and-hold circuit 20, the switch unit 26 is switched to the upper contacts. Thus, switch lever 22 is switched from the lower position as shown, to the upper position, to connect the converter 24 to the sample-and-hold circuit 20. The sample-and-hold circuit 20 is then shifted to the hold condition by the control through connection 38 to continue to store and supply the correction factor through connection 18 to operational amplifier 14 while the digital-to-analog converter 24 is being utilized in the following manner: The switch unit 26 is then shifted back to the position shown, connecting the digital-to-analog converter 24 through the switch element 44 and a connection 46 to a comparison operational amplifier 48. The other input to the comparison amplifier 48 is through a connection 50 from the output of the output amplifier 14. The data processor unit 30 then goes through a successive appproximation program in which digital values are supplied through the digital-to-analog converter 24 starting with the highest order and progressing to the lowest order bits and comparing the output of the digital-to-analog converter 24 in the comparison amplifier 48 with the output 50 to obtain as nearly as possible an exact balance between those two signals. When that exact balance is obtained, the digital values being supplied to the digital-to-analog converter 24 correspond to the analog signal on connection 50. The system then provides that value, converted to binary coded decimal form, through connections at 52 from the data processor interface 28 to a digital display register 54.

Following this operation, switch unit 26 switches back to the upper position to connect the converter 24 to the sample-and-hold circuit 20. The digital correction value is then restored to the digital-to-analog converter 24 and the sample-and-hold circuit 20 is returned to the "sample" mode. Thus, this process is repeated for each successive base line correction signal.

The precise operation of the successive approximation process is as follows: A logic 1 is first inserted in the highest order bit position of the digital-to-analog converter and the resultant signal is compared in the compare circuit 48 with the output from amplifier 14 on connection 50. If the output from the converter 24 is then greater than the measured value on connection 50, that high order bit 1 is converted to a logic 0. If the output from the converter 24 is less than the measured value on connection 50, the one bit is retained. In either case, the next step is to place a logic 1 in the next lower order bit position, and the process is then repeated successively for each lower order bit position until a combination of ones and zeros is determined which come as close as possible to matching the output on connection 50. That is then the value which is displayed in the display register 54, after conversion to decimal form.

The series of base line correction signals which are digitally stored in memory 32 are originally determined by running the liquid chromatograph 10 completely through the desired solvent gradient program without the use of any sample (a "blank" gradient program). This is referred to as a calibration process, or a calibration scan. During this entire calibration scan, the switch unit 26 is maintained in the up position so that the input to the sample-and-hold circuit 20 is from the digital-to-analog converter 24, and the output of amplifier 14 thus is being offset by the digital-to-analog converter output except when the display is being updated as previously mentioned above. That signal is provided through connection 50 to compare amplifier 48. At each correction interval (such as at each half second), the data processor unit 30 operates the digital-to-analog converter and the compare circuit 48 in the successive approximation routine previously described above except that now the input 46 to compare amplifier 48 is grounded by switch 44. By this means, digital values are determined correspondingly exactly to the liquid chromatograph output due to shifts in the absorbence because of changes in the proportions of solvents. These are then the correct baseline correction values to be subtracted from the later regular run of the liquid chromatograph with a sample in order to get a flat zero-corrected base line.

In accordance with another important feature of this invention, the first base line correction signal (at point 1) has a special status and is stored in a special position in memory. That first correction value is then used in a special process at the very beginning of each regular scan with a sample. This special process is for the purpose of introducing a drift correction. This is accomplished as follows:

At the first correction interval, generally before any appreciable sample signal is expected, a reading is taken in the calibration scan mode, with the switch 26 in the up position and using the digital-to-analog converter 24 and the compare amplifier 48 in a successive approximation program to derive a new base line correction for the very first correction point (point 1). The prior first (point 1) base line correction signal digital number from the calibrate scan is then subtracted from the new point 1 base line correction number and the difference is stored in memory 32. That difference is a drift offset correction factor which indicates the drift of the system. The drift offset correction factor is then added to each base line correction signal in order to correct the entire base line for drift.

Figure 2:
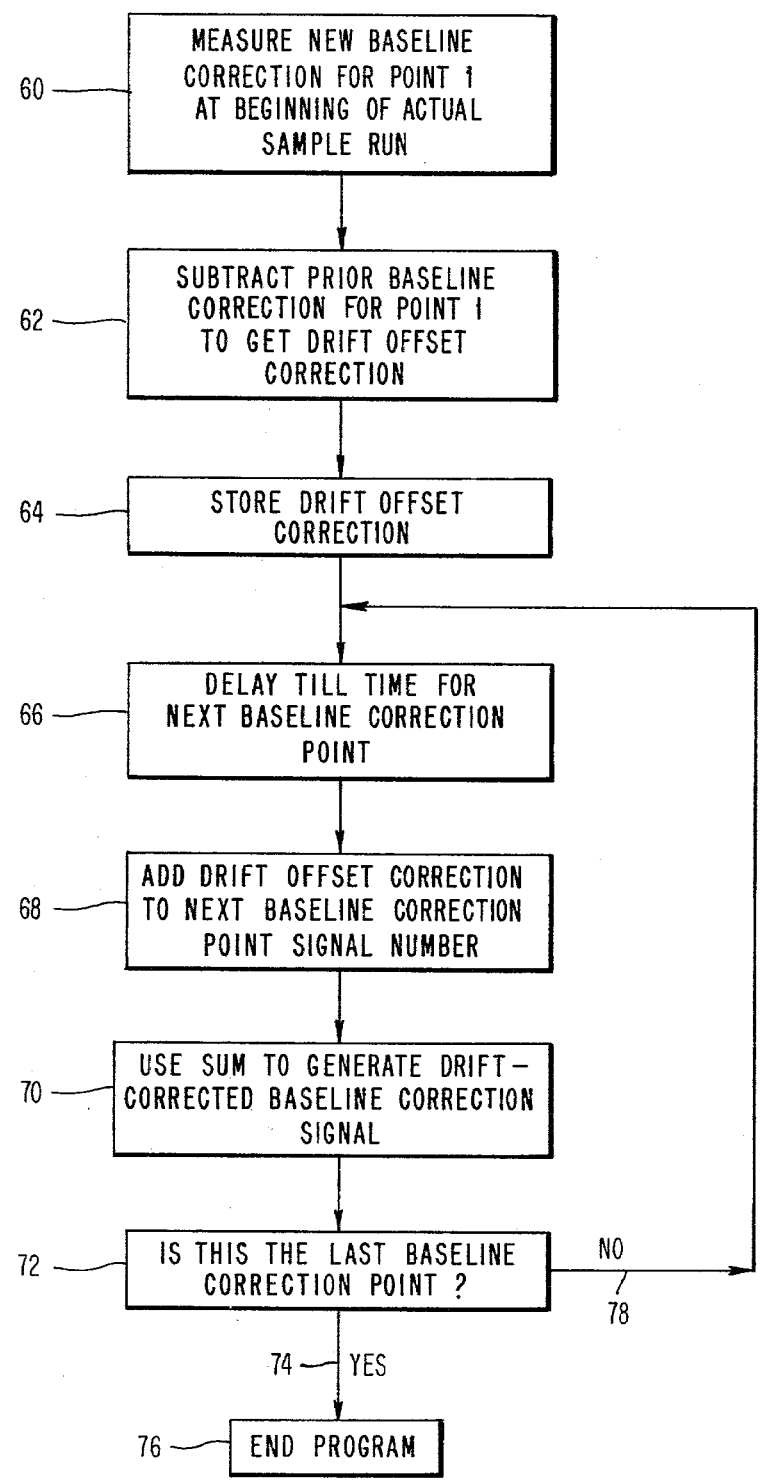
FIG. 2 is a flow chart showing one aspect of the operation of the invention which particularly pertains to the correction of drift offset.

The above described process is shown in more detail in the flow chart of FIG. 2 wherein the first step at box 60 calls for measurement of the new base line correction for point 1 at the beginning of the actual sample run. The second step 62 involves the subtraction of the prior base line correction for point 1 to get the drift offset correction. In the third step 64, the drift offset correction is stored.

In the fourth step 66, there is a delay until it is time for the next base line correction point. In the fifth step 68, the drift offset correction is added to the next base line correction point signal number to obtain a drift corrected sum. In the next step 70, that sum is used to generate a drift corrected base line correction signal in the digital-to-analog converter 24. In the next step, indicated at 72, a test is made to determine whether this was the last base line correction point. If the answer is "Yes", as indicated by a signal at 74, the program is ended, as indicated at 76. If the answer is "No", as indicated by a signal at 78, the process loops back to the step indicated at 66, and the steps 66-72 are repeated. By means of this process, the system is constantly corrected for drift, at least as often as the beginning of each sample run.

Figure 3:
FIG. 3 illustrates an uncorrected chromatogram made without the benefit of the base line correction feature of the present invention.
Figure 4:
FIG. 4 is a corrected chromatogram corresponding precisely with FIG. 3, and illustrating the benefits of the base line correction accomplished in accordance with the present invention.

FIG. 3 and FIG. 4 illustrate how effective the present invention can be in providing full base line correction. FIG. 3 illustrates an actual chromatogram trace without base line correction during a hexane to chloroform solvent gradient program using ultraviolet light at 250 nm. An extreme base line shift is experienced because chloroform absorbs ultraviolet light at 250 nm, while hexane does not.

FIG. 4 illustrates an actual chromatogram using the same solvents and the same solvent gradient and the same sample (o-dinitrobenzene and trinitrobenzene) as in FIG. 3, but with the base line correction provided by the present invention. This base line correction has been found to be so effective that extremely high sensitivities may be employed which, without the correction, would result in off-scale conditions.

It is one of the features of the invention that, having once run the calibration cycle and having stored base line correction numbers in memory 32, those numbers can be used to generate appropriate base line correction signals at different chart speeds and attenuations (or amplifications) of operation of the recorder 16, as long as the same liquid gradient program is used. Thus, having established the full base line correction, the sample can be re-run at higher sensitivities in order to provide higher sensitivity and more meaningful outputs.

The base line correction available with the system of the present invention has been found to be extremely sensitive and responsive. Thus, it is possible to reverse the procedure described above and to run the calibrate cycle *with a sample*, and to store all of the separation sample values, along with the base line correction values in the memory 32. The system is then operated in the regular run mode without a sample. This results in a display which is reversed, since the separation signal values are stored with the base line correction signals as subtractive signals. If desired, these stored sample values may be re-run with changes in system sensitivity for repeated analysis of data where only one sample could be run. This procedure is very useful where the amount of the sample is very limited.

The central data processor unit 30 of FIG. 1, which is sometimes referred to below as a "control means", may be conveniently implemented in the form of a standard microprocessor unit such as the Motorola Model 6802. For the memory 32, ten type 2114 random access memories (RAMS) may be employed which are available from any one of a number of different vendors, including Intel. The peripheral interface adaptor 28 may be a Motorola circuit type 6821. However, other microprocessors, interfaces, and memories may be employed.

While FIG. 1 shows the spectrophotometer 11 and the remainder of the system as physically separated, it is possible that all of the components of the system illustrated in FIG. 1, exclusive of the liquid chromatograph 10 and the chart recorder 16, be incorporated with the spectrophotometer in a common housing.

While this invention has been shown and described in connection with a particular preferred embodiment, it is apparent that various changes and modifications, in addition to those mentioned above, may be made by those who are skilled in the art without departing from the basic features of the invention. Accordingly, it is the intention of the applicant to protect all variations and modifications within the true spirit and valid scope of this invention.

We claim:

1. A liquid chromatography system for performing programmable solvent gradient scans, comprising
    a liquid chromatograph,
    a spectrophotometer connected to said chromatograph,
    and apparatus for compensating for base line shift as the proportions of solvents are changed comprising
    a digital data memory for storing a series of digital numbers representing the required values of base line shift correction signals at spaced time intervals during a solvent gradient program,
    control means for reading out said digital numbers in sequence at spaced time intervals,
    a digital-to-analog converter connected to receive said base line shift correction signal numbers and to convert each number to a corresponding base line correction signal voltage,
    a sample-and-hold circuit,
    switch means for connecting the voltage from said digital-to-analog converter to said sample-and-hold circuit at spaced time intervals as different base line shift correction signals are available at the output of said digital-to-analog converter, and
    an offset amplifier having at least two input signals,
    one input signal to said offset amplifier being received from said spectrophotometer,
    the other input signal of said offset amplifier being received from said sample-and-hold circuit for subtracting the base line shift correction signals stored within said sample-and-hold circuit from the signals received from said spectrophotometer,
    the output of said offset amplifier comprising the base line shift corrected output of said liquid chromatography system.

2. Apparatus as claimed in claim 1 further comprising:
    a comparison amplifier having at least two inputs; and wherein
    said switch means is operable to disconnect said digital-to-analog converter from said sample-and-hold circuit when conversion of the output of said offset amplifier to digital numbers is made for display,
    said switch means being operable to connect said digital-to-analog converter to one input of said comparison amplifier when disconnecting said digital-to-analog converter from said sample-and-hold circuit,
    the other input of said comparison amplifier being connected to receive the output of said offset amplifier,
    said control means being operable in a successive approximation mode to cause said digital-to-analog converter to have a digital input value which provides an output signal voltage which balances with said system output voltage at said comparision amplifier so that the digital input signal to said digital-to-analog converter corresponds in magnitude to said system output voltage,
    said control means being operable to convert the balanced digital input value supplied to said digital-to-analog converter to a corresponding decimal number for display,
    and a decimal display unit connected to receive and display the decimal number as visible indication of the system output signal.

3. A system as claimed in claim 1 wherein there is included
    a comparison amplifier having at least two inputs,
    said apparatus being operable in a calibrate mode,
    said switch means being operable when in the cailbrate mode to connect said digital-to-analog converter to said sample-and-hold circuit,
    said switch means being operable when in the calibrate mode to connect one input of said comparison amplifier to ground,
    the other input of said comparison amplifier being connected to receive the output of said offset amplifier,
    and said control means being operable by use of said comparison amplifier in a successive approximation mode to cause said digital-to-analog converter to have a digital input value which provides an output signal voltage which balances with said system output voltage so that the digital input signal to said digital-to-analog converter corresponds in magnitude to said system output voltage during a calibrate cycle when the system is run without a sample,
    said control means being operable to store the balanced digital input value supplied to said digital-to-analog converter in said digital memory as a base line shift correction signal number,
    and said control means being operable to repeat the above-mentioned operation at spaced time intervals to store a series of base line shift correction numbers.

* * * * *